(12) United States Patent
East et al.

(10) Patent No.: US 9,378,661 B2
(45) Date of Patent: *Jun. 28, 2016

(54) SPINAL INJECTION TRAINER AND METHODS THEREFOR

(71) Applicant: BIOTRAS HOLDINGS, LLC, Addison, TX (US)

(72) Inventors: Johnny Wayne East, Fort Worth, TX (US); Brandon Knutson, Addison, TX (US); Edwin V. East, Jr., Addison, TX (US)

(73) Assignee: BioTras LLC, Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/818,137

(22) Filed: Aug. 4, 2015

(65) Prior Publication Data

US 2015/0339954 A1 Nov. 26, 2015

Related U.S. Application Data

(63) Continuation-in-part of application No. 14/325,391, filed on Jul. 8, 2014.

(60) Provisional application No. 61/847,564, filed on Jul. 18, 2013.

(51) Int. Cl.
| | |
|---|---|
| G09B 23/28 | (2006.01) |
| G09B 23/30 | (2006.01) |
| G09B 23/34 | (2006.01) |
| A61B 17/16 | (2006.01) |

(52) U.S. Cl.
CPC .......... *G09B 23/285* (2013.01); *A61B 17/1671* (2013.01); *G09B 23/30* (2013.01); *G09B 23/34* (2013.01)

(58) Field of Classification Search
USPC .......................................... 434/267, 272, 274
See application file for complete search history.

(56) References Cited

U.S. PATENT DOCUMENTS

| | | | |
|---|---|---|---|
| 2,207,153 A | 7/1940 | Judovich | |
| 2,689,415 A * | 9/1954 | Haver ................ | G09B 23/285 434/272 |

(Continued)

OTHER PUBLICATIONS

Jia Wei Li, Mphill, Manoj K. Karmakar, Md, Xiang Li, PhD, Wing Hong Kwok, Fanzca and Warwick Dean Ngan Kee, Md; Gelatin-Agar Lumbosacral Spine Phantom; Journal of Ultrasound in Medicine, Feb. 1, 2011, vol. 30, No. 2 263-27, www.jultrasoundmet.org.

(Continued)

*Primary Examiner* — Xuan Thai
*Assistant Examiner* — James Hull
(74) *Attorney, Agent, or Firm* — Howison & Arnott, LLP

(57) ABSTRACT

A model for anatomical training includes a visibly clear thermoplastic elastomer matrix formed with at least one contoured surface, the contoured surface simulating at least a portion of a human body. The visibly clear thermoplastic elastomer matrix provides visible needle tracks upon needle penetration that may be fused closed upon heating the thermoplastic elastomer matrix such that the needle tracks are no longer visible. The model includes a skeletal structure embedded within the thermoplastic elastomer matrix at the same location, relative to the contoured surface, as the corresponding skeletal structure is located in a human body, the skeletal structure producing a fluoroscopic image representative of human bone corresponding to the skeletal structure.

20 Claims, 9 Drawing Sheets

(56) References Cited

U.S. PATENT DOCUMENTS

| | | | |
|---|---|---|---|
| 6,780,016 B1 | 8/2004 | Toly | |
| 7,866,984 B1 | 1/2011 | Jawalekar | |
| 8,403,675 B2 | 3/2013 | Stoianovici et al. | |
| 9,017,080 B1 * | 4/2015 | Placik | G09B 23/285 |
| | | | 434/269 |
| 2005/0035282 A1 * | 2/2005 | Lehmann | A61N 5/1048 |
| | | | 250/252.1 |
| 2005/0106545 A1 | 5/2005 | Heruth et al. | |
| 2006/0191544 A1 | 8/2006 | Simmonds et al. | |
| 2007/0290446 A1 * | 12/2007 | Amick | A61L 15/225 |
| | | | 273/404 |
| 2009/0142741 A1 | 6/2009 | Ault et al. | |
| 2010/0055657 A1 * | 3/2010 | Goble | G09B 23/286 |
| | | | 434/262 |
| 2010/0167254 A1 * | 7/2010 | Nguyen | G09B 23/30 |
| | | | 434/272 |
| 2010/0269581 A1 * | 10/2010 | Giurintano | F42B 35/00 |
| | | | 73/167 |
| 2010/0311025 A1 | 12/2010 | Everett | |
| 2012/0034587 A1 | 2/2012 | Toly | |
| 2013/0045469 A1 * | 2/2013 | Noras | A61B 5/061 |
| | | | 434/262 |
| 2014/0272873 A1 * | 9/2014 | Svensson | G09B 23/34 |
| | | | 434/268 |

OTHER PUBLICATIONS

NASCO (Fort Atkinson) Plastics; Lifeform: Spinal Injection Simulator LF01036U Instruction Manual; NP 161-83/RV 7-15; 6 pages; www.enasco.com.

Epimedpain.com; Genesis Epidural-Spinal Injection Simulator; http://www.epimedpain.com/productdetails.php?productid=118&categoryid=3&subcategoryid=47; retrieved Sep. 23, 2015.

* cited by examiner

SPINAL INJECTION TRAINER AND METHODS THEREFOR

CROSS-REFERENCE TO RELATED APPLICATIONS

This application is a Continuation-In-Part of U.S. patent application Ser. No. 14/325,391, filed on Jul. 8, 2014, entitled SPINAL INJECTION TRAINER AND METHODS THEREFOR, which claims benefit of U.S. Provisional Application No. 61/847,564, filed on Jul. 18, 2013, entitled SPINAL INJECTION TRAINER AND METHODS THEREFOR. U.S. patent application Ser. No. 14/325,391 and 61/847,564 are incorporated herein by reference in their entirety.

TECHNICAL FIELD

The present invention relates generally to medical training models and more particularly to a model that includes natural vertebrae embedded in a matrix of clear synthetic ballistic gel, and its uses.

BACKGROUND

While use of cadavers has been declining in U.S. Medical schools primarily due to cost of preparing and maintaining the corpus, anatomists have complained that cadavers are still the best way to teach anatomy because it provides kinesthetic reinforcement as opposed to computerized models. Although anatomical teaching models are better now than in the past, a common material used to simulate tissue, silicone, although superior to other less resilient plastics, still does not provide the tactility of human tissue.

Spinal models for injection technique practice or training have been described in the past. Computerized Imaging Reference Systems, Inc, Norfolk Va., offers a lumbosacral spine model that includes a radiopaque plastic spinal model embedded in silicone. Other models including natural gelatin based embedded spinal phantoms for ultrasound use have been described; Jia Wei et al. "Gelatin-Agar Lumbosacral Spine Phantom" J Ultrasound Med (2011) 30:263-272, describes an agar-gelatin matrix and Bellingham et al., "A Low-Cost Ultrasound Phantom of the Lumbosacral Spine" Regional Anesthesia and Pain Medicine (2010) vol. 35, no. 3, describes a concentrated gelatin matrix. However, neither silicone models nor the described natural gelatin based matrices provide realistic tactile feedback for the trainee.

Natural gelatin is a material obtained from collagen and other animal by-products and is a component in numerous foods and cosmetic products. More particularly, "ballistic" gel is a formulation based on either natural gelatin or a synthetic, which is calibrated to possess ideally, characteristics similar to human muscle tissue, and is used primarily in ballistics testing. One standard calibration of ballistic gel involves firing into it a .177 caliber steel BB, from an air gun, measuring the velocity of the projectile and the depth of penetration. Ballistic gels based on natural gelatin will darken, degrade quickly, and cannot be reused. Because bacterial contamination and decay are a concern, natural gelatin based models must be refrigerated between uses. While training phantoms employing skeletal replicas are adequate for sonographically guided needle insertion, plain plastic or resin components will not show adequately in either plain x-ray or fluoroscopic imaging because they are non-radiopaque. In the case of x-rays, bone appears lighter than the surrounding tissue. In a fluoroscope, relatively more x-rays pass through soft tissue to fluoresce on a phosphor screen and produce real time moving images wherein the bones appear relatively darker than the surrounding tissue. While some practice models employ plastic vertebrae made of radiopaque resin enabling it to be seen in a fluoroscope monitor, the image contrast provided by radiopaque plastic is unlike that of natural bone because of the naturally non-uniform distribution of calcium in bone which selectively absorbs more or less of the x-rays, thereby producing a more dimensional image.

Both silicone "tissue" of costly training models and the relatively inexpensive gelatin based phantoms break down with repeated punctures rendering them unfit for training. At some point, accumulated needle tracks will interfere with both light transmission, clarity and disturb the intended path and placement of subsequent needles. It would be desirable to provide a teaching model for the human spine that provides realistic tactile feedback of the vertebral column and surrounding tissue. It would be further desirable if such models were suitable for fluoroscopically guided spinal injection techniques. In addition to being reusable and requiring no refrigeration, the foregoing model should produce an image that reflects actual natural bone contour, and be transparent so that needle path and placement can be observed or practiced with or without the use of imaging techniques such as fluoroscopy or sonography.

SUMMARY

The present invention seeks to address the shortcomings of past spinal training models by providing a spinal model that includes a complete vertebral column that is embedded in a matrix of crystal clear ballistic gel. The synthetic gel does not harbor bacteria, can be reused and does not require refrigeration. Natural bone typically provides better image contrast than synthetic radiopaque replicas. More dimensional, i.e., contoured image contrast, is obtainable with natural bone which is obtained via cadavers or antique teaching skeletons. For use in training needle techniques such as spinal anesthesia and or lumbar epidural steroid injections, a transparent synthetic gel matrix permits observation of needle progression by both the trainee and the trainer and provides unique opportunities for coaching and intercession to prevent poor needle placement prior to its occurrence. Because the matrix closely simulates the feel of human tissue, for purposes of anatomy instruction, a flexible opaque sheet of a self-healing material such as closed cell polyurethane foam or similar material, having a thickness between 2 and 10 mm, may be placed over the model so that the structures and regions of the spine can be taught, and later independently discerned, without benefit of visual reinforcement.

In one embodiment, a model for anatomic training and injection practice includes a visibly clear thermoplastic elastomer matrix formed with at least one contoured surface. The contoured surface simulates at least a portion of a human body while the visibly clear thermoplastic elastomer matrix provides visible needle tracks upon needle penetration. The visible needle tracks are fused closed upon heating the thermoplastic elastomer matrix such that the needle tracks are no longer visible in the thermoplastic elastomer matrix. A skeletal structure is embedded within the synthetic gel matrix at the same location, relative to the contoured surface, as the corresponding skeletal structure is located in a human body. The skeletal structure is selected to produce a fluoroscopic image representative of human bone corresponding to the skeletal structure. The visibly clear thermoplastic elastomer matrix provides tactile feedback substantially similar to human tissue. The model may include a form for receiving the visibly clear thermoplastic elastomer matrix and skeletal structure, the form having contoured portions simulating surfaces of at least a portion of a human body. In one embodiment, at least a portion of the skeletal structure is natural human bone.

In one aspect, a selected portion or portions of the visibly clear thermoplastic elastomer matrix may be replaced by removing the selected portion, replacing the removed selected portion with a new replacement portion and applying heat to fuse the replacement portion into the model. The model may also include at least one heat source embedded in the visibly clear, thermoplastic elastomer matrix to provide localized heating of a portion of the visibly clear thermoplastic elastomer matrix to fuse needle tracks formed in the matrix. The heat source may be positioned adjacent to one or more portions of the vertebral column, for example, adjacent the vertebral column.

The model may also include one or more embedded light sources, for example a plurality of LEDs, whereby the light source increases the visibility of needle tracks formed in the visibly clear thermoplastic elastomer matrix. The light source may be embedded in the visibly clear thermoplastic elastomer matrix adjacent at least a portion of the skeletal structure, for example, the vertebral column, to enhance viewing of needle tracks resulting from needle penetration in the region of the matrix surrounding the skeletal structure.

In another aspect, the embedded skeletal structure may be a partial or complete vertebral column. The model may also include synthetic simulated soft tissue structure such as one or more synthetic intervertebral discs, a simulated spinal cord and simulated spinal nerves. The model may also include surgical hardware installed, for example, on the embedded vertebral column and a heat source embedded in the synthetic gel matrix adjacent at least a portion of the vertebral column to provide localized heating of a portion of the visibly clear thermoplastic elastomer matrix to fuse needle tracks formed in the matrix and/or fuse a replacement portion of the matrix. Radiopaque markers may be embedded in the visibly clear thermoplastic elastomer matrix adjacent selected portions of the skeletal structure. The radiopaque markers may serve as targets for needle insertion practice.

In one variation, the visibly clear thermoplastic matrix comprises from about 15 wt % to about 20 wt % of a rubbery block copolymer and from about 80% to about 85% of a white oil. The rubbery block copolymer may comprise an SEBS (styrene-ethylene/butylene-styrene) block copolymer. In one embodiment, the rubbery block copolymer has a tensile stress of from about 8.00 to about 10 psi, a tensile strength at break of from about 140 to about 170 psi and a tensile elongation at break of from about 500 to about 1500%.

DETAILED DESCRIPTION

Figure 1:
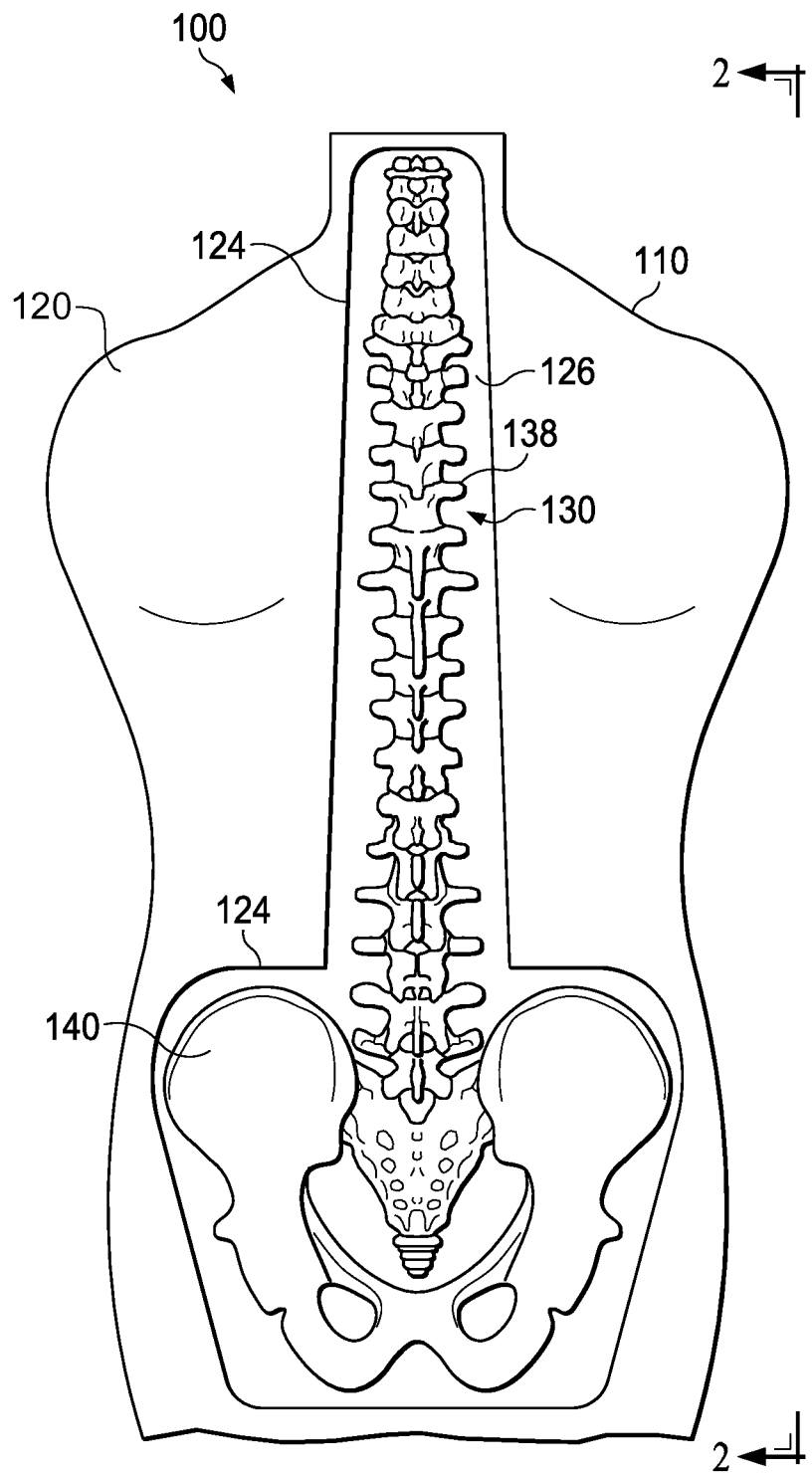
FIG. 1 is a top view of a first embodiment a spinal injection trainer according to the disclosure.
Figure 2:
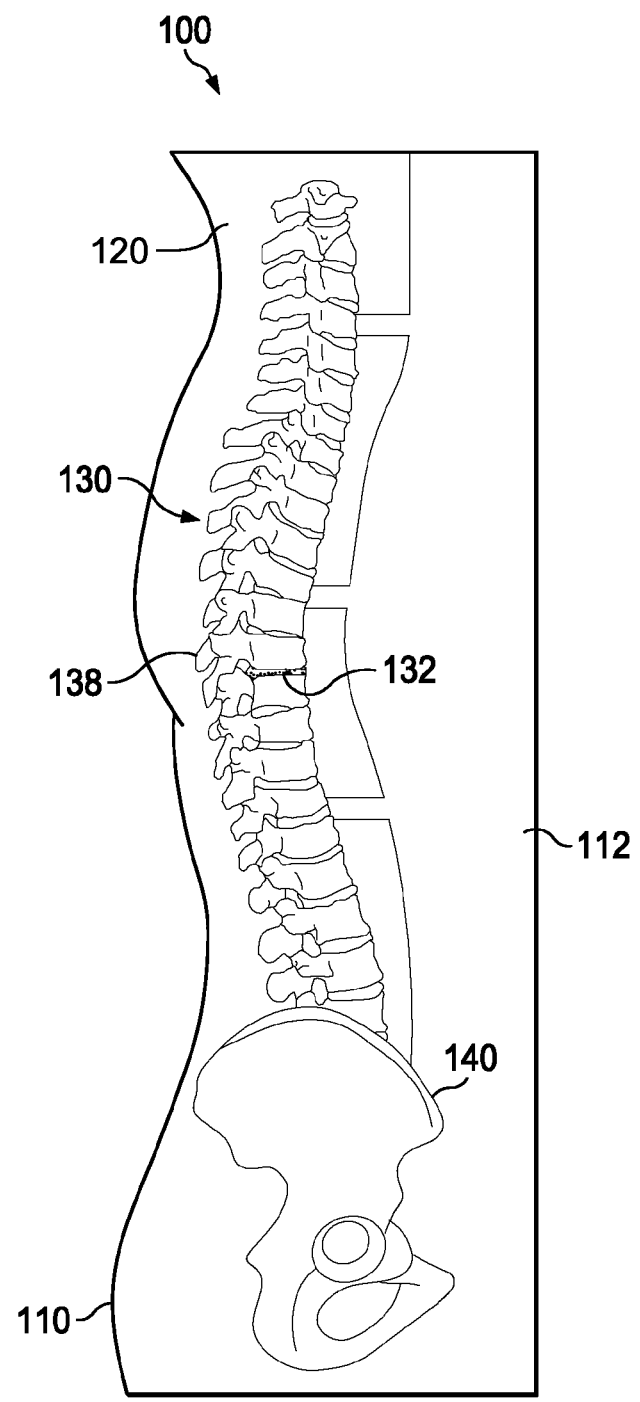
FIG. 2 is a lengthwise cross-sectional view taken along lines 2-2 of the embodiment shown in FIG. 1.

FIGS. 1 and 2 are partial top and side views of a spinal injection training model 100. As illustrated, model 100 includes a complete vertebral column 130 and pelvic bone 140 embedded in synthetic gel matrix 120 along with simulated intervertebral discs 132. In one embodiment, matrix 120 is a transparent synthetic ballistic gel having a density and feel substantially similar to that of human tissue in order to provide realistic haptic feedback upon needle insertion and placement. The transparent synthetic ballistic gel also provides realistic haptic feedback during spinal palpation practice. The synthetic gel does not harbor bacteria, can be reused and does not require refrigeration. Synthetic ballistic gels have been formulated to have some of the properties of natural gelatin, but are odorless and colorless, and unlike natural gelatin, can be reused by heating and reforming by melting and re-pouring into a form. Two U.S. companies that make or sell synthetic ballistic gel are Clear Ballistics LLC., P.O. Box 723, Fort Smith, Ark. 72901, and Ballistek Gel LLC, N8547 North Rd, Ixonia, Wis. 53036. In different embodiments, other materials simulating the feel of human tissue may be used.

One material suitable for use as synthetic gel matrix 120 is a visibly clear thermoplastic elastomer comprising approximately 15 wt % of a rubbery block copolymer with approximately 85 wt % of white oil. In one embodiment, 16.6 wt % SEBS (styrene-ethylene/butylene-styrene) block copolymer is mixed with 83.4 wt % of a white oil and the mixture is heated to approximately 250° F. and allowed to cool. Upon cooling, the mixture forms a clear, thermoplastic elastomer suitable for use as synthetic gel matrix 120. A suitable material for use as synthetic gel matrix 120 has a specific gravity of 0.87 (ASTM D792), a tensile stress of 9.00 psi (ASTM D412), a tensile strength at break of 154 psi (ASTM D412), a tensile elongation at break of 1300% (ASTM D412), a tear strength of 40 lbf/in (ASTM D624), a durometer hardness of 30 (Shore 00, 10 sec, ASTM D2240) and an apparent viscosity of 1.30 Pas (392° F., 11200 sec^-1 ASTM D3835). The material is water clear and has a texture and feel that simulates human tissue.

In different embodiments, synthetic gel matrix 120 may comprise a thermoplastic elastomer comprising from about 15 to about 20 wt % of an elastomeric block copolymer such as an SEBS (styrene-ethylene/butylene-styrene) block copolymer mixed with from about 80 to about 85 wt % of a white oil. Suitable materials for use as synthetic gel matrix 120 may have a specific gravity of from about 0.80 to about 0.90 (ASTM D792), a tensile stress of from about 8.00 to about 10 psi (ASTM D412), a tensile strength at break of from about 140 to about 170 psi (ASTM D412), a tensile elongation at break of from about 500 to about 1500% (ASTM D412), a tear strength of from about 30 to about 50 lbf/in (ASTM D624), a durometer hardness of from about 25 to about 35 (Shore 00, 10 sec, ASTM D2240) and an apparent viscosity of from about 1.20 to about 1.40 Pas (392° F., 11200 sec^-1 ASTM D3835). Such materials will have a density and elastic properties that provide a feel, texture and resistance to needle insertion similar to human tissue.

A form or mold 110 containing matrix 120 includes an upper opening 124 that exposes a portion of the upper surface 126 of synthetic gel matrix 120 for needle insertion practice. Mold 110 may be formed from a rigid material such as an acrylic, a polycarbonate or a metal. In some applications, model 100 may be transported or stored in mold 110 to protect the model. In different embodiments, mold 110 may be partially contoured to simulate the surfaces of a partial or complete human torso, a torso with a head and neck, or any desired portion of a human body, depending upon the particular application. In the embodiment illustrated in FIGS. 1 and 2, mold 110 is contoured on one side to simulate the surface of the back of a human torso while in other embodiments mold 110 may be contoured to simulate a complete human torso.

In one embodiment, vertebral column 130 is natural bone, in other embodiments vertebral column 130 may be formed from materials that provide contrast during fluoroscopic imaging that simulates or is representative of human bone. In an embodiment where vertebral column 130 is human bone, the vertebral column may be obtained from cadaverous specimens, or from antique skeletal models. To prepare the model, vertebrae 138 are first cleaned and treated with a sealant that is non-reactive with the thermoplastic elastomer matrix 120 and placed in contoured form 110 (mold) with the spinous processes pointing down, with the vertebral body facing up. Vertebral column 130 and pelvic bone 140 may be secured from shifting during the molding process with a jig or similar support structure or by other suitable means. In one embodiment, an insert 112 may be utilized to secure vertebral column 130 and pelvic bone in position during the molding process. Vertebral column 130 is embedded within synthetic gel matrix 120 at the same location, relative to the contoured surfaces of model 100, as the corresponding skeletal structure is located in a human torso. Since the bottom inside surface of mold 110 is contoured to resemble the curves of the human back, a uniform distance of about 2 cm will exist between the tops of spinous processes and the mold bottom.

One or more blocks of synthetic ballistic gel are placed into the mold void containing vertebral column 130 which is then heated in an oven to melt and fuse the gel. Once liquefied, the matrix may be subjected to vibration to raise trapped air to the surface. After the gel cools and firms, the top or upper surface of model 100 can be trimmed with a knife or wire to remove any bubbles. It is possible, of course to apply a vacuum for degassing the matrix to draw out trapped or entrained air, preferably prior to curing. In other variations, the synthetic gel may be melted in a separate container and then poured into mold 110 and allowed to solidify. After the synthetic gel has solidified, mold 110 may be removed from model 100. In some embodiments it may be desirable to leave model 100 in mold 110 for transportation or storage and/or provide one or more openings, such as opening 124, for access to the model.

Figure 3:
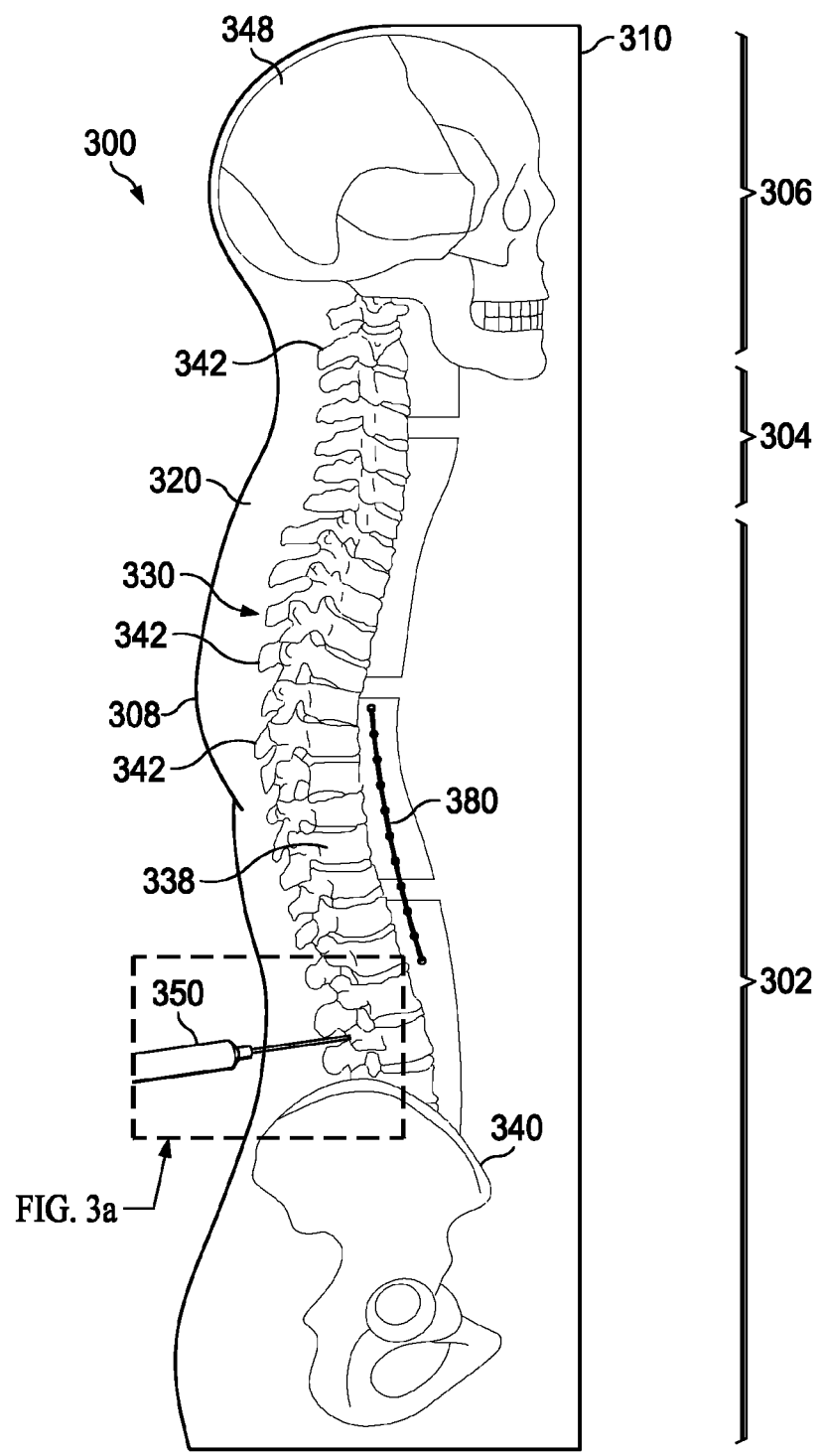
FIG. 3 is a side view of a second embodiment of a spinal injection trainer illustrating a needle insertion.

FIG. 3 is a side view of a second embodiment of a model 300 including a torso section 302, a neck section 304 and head section 306. A complete vertebral column 330, skull 348 and pelvic bone 340 are imbedded in synthetic gel matrix 320. Forming model 300 with neck section 304 and head section 306 provides a more realistic model for training purposes and is also useful in connection with chiropractic training and practice. In an embodiment where one or more complete vertebral column 330, skull 348 and pelvic bone 340 are natural bone, the contrast produced during a fluoroscopically-guided procedure will realistically simulate that of an actual in vivo procedure. In other embodiments a suitable synthetic material that provides contrast representative of natural bone may be employed to form skeletal structures. As illustrated the back or dorsal side 308 of model 300 is contoured to correspond to the typical contours of a human back, neck and head with the contour of the torso portion following the spinous processes 342 of vertebrae 338.

Model 300 may be molded and formed in the same or in a similar manner as described in connection with model 100. As illustrated, the front surface 310 of model 300 is essentially flat which provides a stable surface upon which the model may be placed, with a back (dorsal) surface contoured to match a human torso. Alternatively, model 300 could be molded with contours corresponding to the front, back and sides of the torso, neck and head of a typical human body. Model 300 could also be molded to correspond to a lesser or greater portion of a typical human body depending upon the particular use and application. Vertebral column 330, skull 348 and pelvic bone 340 are positioned in synthetic gel matrix 320, relative to the contoured surfaces of model 300, as the corresponding skeletal structure is positioned within a human body. Model 300 may be supplied in various sizes corresponding to different body types including obese body types, in which case synthetic gel matrix 320 would have a relatively greater thickness over spinous processes 342. This is particularly useful in chiropractic training as palpation of the spinal elements is key.

Figure 3A:
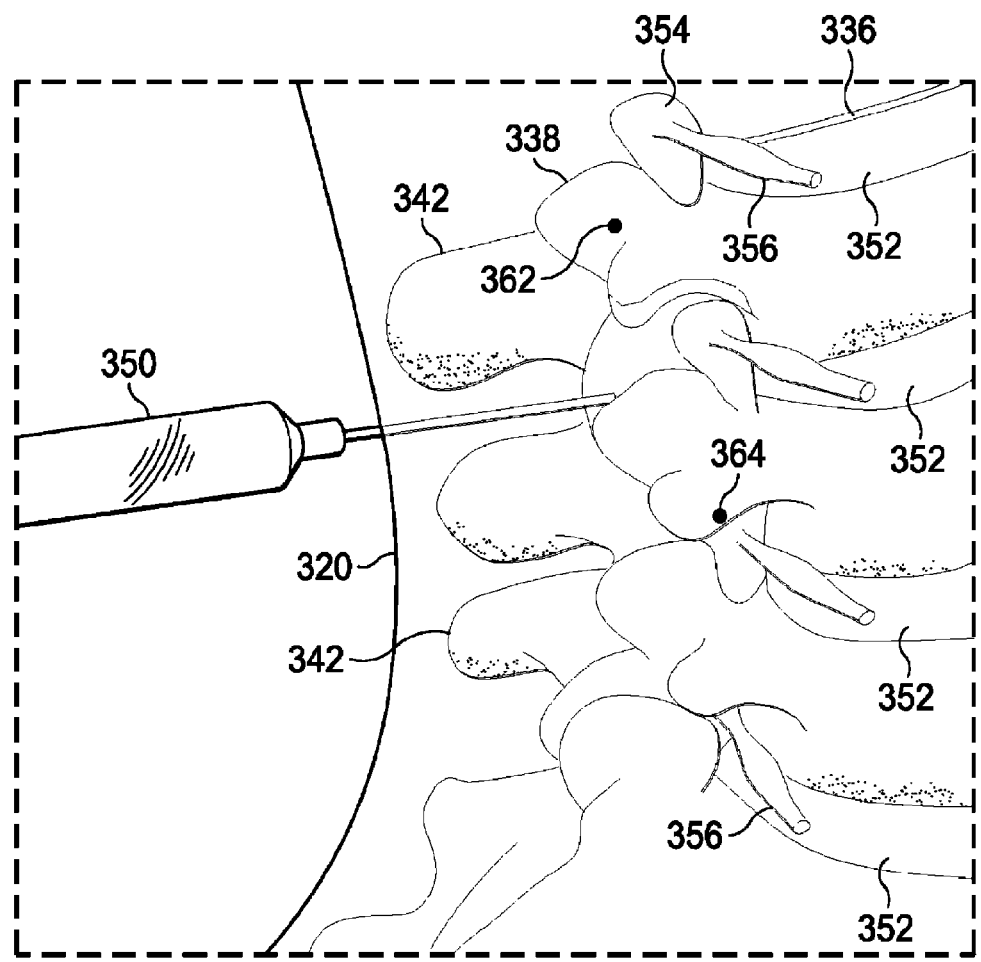
FIG. 3A is a detail view of a segment of spinal column of FIG. 3 illustrating foam discs positioned between vertebrae.

FIG. 3A is a detail view of the insertion of a needle 350 between vertebrae 338 such that the injection technique can be observed from any direction. As illustrated, a section of vertebral column 330 is provided with artificial foam discs 352 to simulate actual vertebral discs. Artificial foam discs 352 may be formed from urethane foam, silicone, or other suitable material that simulates the density of a human vertebral disc. Artificial foam discs 352 provide haptic feedback during needle insertion training as the force required to continue insertion of the needle from synthetic gel matrix into one of the artificial foam discs 352 will change when the needle penetrates the artificial foam disc. In one embodiment, foam discs 352 are formed with a silicone layer 336 on the upper and lower surfaces of the disc. Alternatively, foam discs 352 may be embedded in, or covered with, a silicone or urethane of a different density. In one embodiment, a simulated spinal cord 354 and a simulated spinal nerve 356 are embedded in synthetic gel matrix 320. Simulated spinal cord 354 and simulated spinal nerve 356 may be formed from a silicon or similar material to simulate actual tissue.

In some applications it may be desirable to provide a marker or "target" for spinal injection training purposes. FIG. 3A illustrates the placement of radiopaque markers 362, 364 that may be used as targets for needle injection practice. Marker 362 corresponds to a target for a lumbar medial block injection and marker 364 serves a target for a lumbar transforaminal injection. Markers 362, 364 may be used as a guide during a fluoroscopically-scanned practice injection. Alternatively, a needle may be inserted into model 300 and, after insertion, a fluoroscopic scan may be used to determine how close to the target the tip of the needle was placed.

Figure 3B:
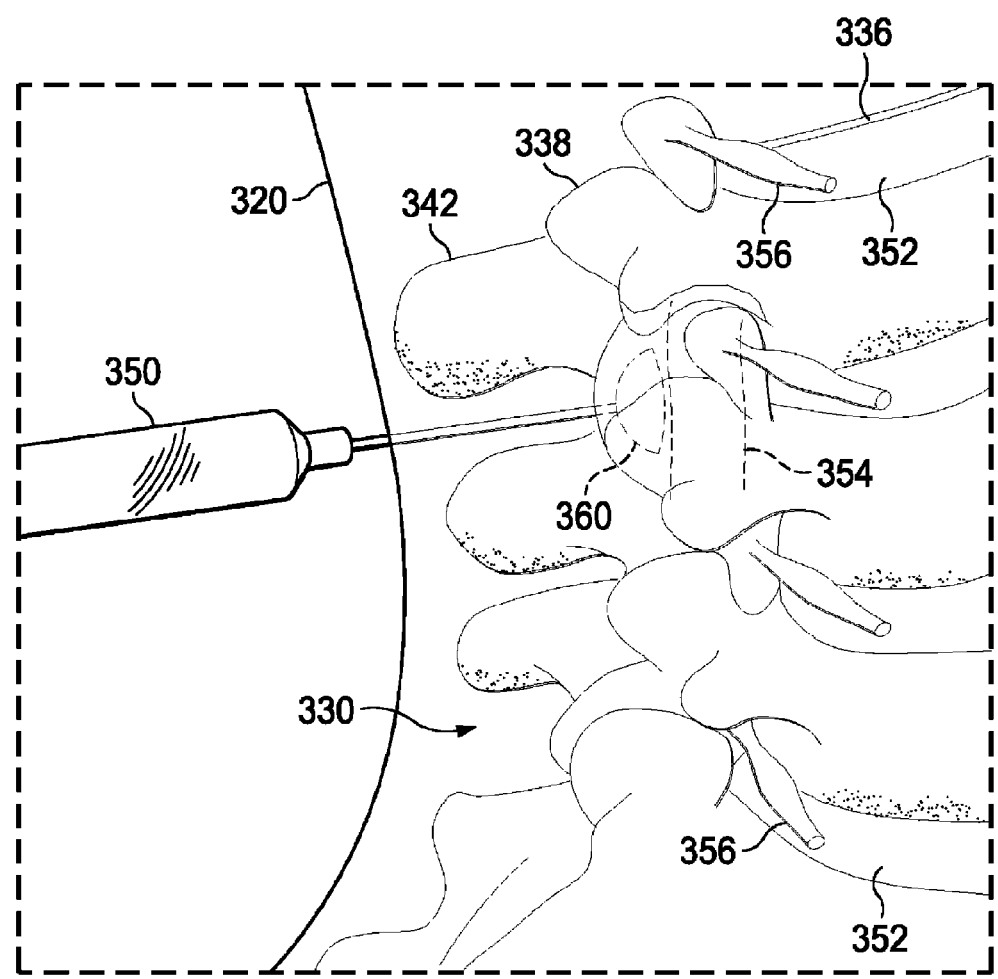
FIG. 3B is a detail view of a segment of spinal column of FIG. 3 illustrating the formation of a simulated epidural space.

Referring now to FIG. 3B, in one embodiment, a simulated epidural space 360 or void may be created in model 300. To form epidural space 360, needle 350 is connected to a source of compressed air (not shown) or suitable gas such as nitrogen and inserted to the desired location in vertebral column 330. Air is metered through needle 350 to create a bubble in synthetic gel matrix 320 at the desired location. In one variation, needle 350 is inserted through synthetic gel matrix 320 after model 300 has been molded, but before the synthetic gel has solidified, e.g., as the gel cools after molding. Simulated epidural space 360 provides haptic feedback during needle insertion training as the force required to continue insertion of the needle from the synthetic gel matrix 320 into the simulated epidural space will change when the needle penetrates the simulated epidural space.

Referring again to FIG. 3, in one embodiment, a light source 380 is embedded in synthetic gel matrix 320 of model 300. Light source 380 may be a plurality of LEDs, for example a linear strip of LEDs or a similar light source connected to an external power source (not shown). As illustrated, light source 380 is positioned adjacent a portion of vertebral column 330 on the anterior side of the column. In different embodiments light source 380 may be positioned on the dorsal side of vertebral column 330 or laterally on one or both sides of the column. Light source(s) 380 may be positioned adjacent only a selected portion of vertebral column 330, at several locations along column 330, or a plurality of light sources may be used to illuminate the entire model, including skull 348, vertebral column 330 and pelvic bone 340. Light from light source 380 is diffused by synthetic gel matrix 320 and serves to illuminate a needle during insertion practice and to illuminate needle tracks formed during needle insertion.

Figure 4:
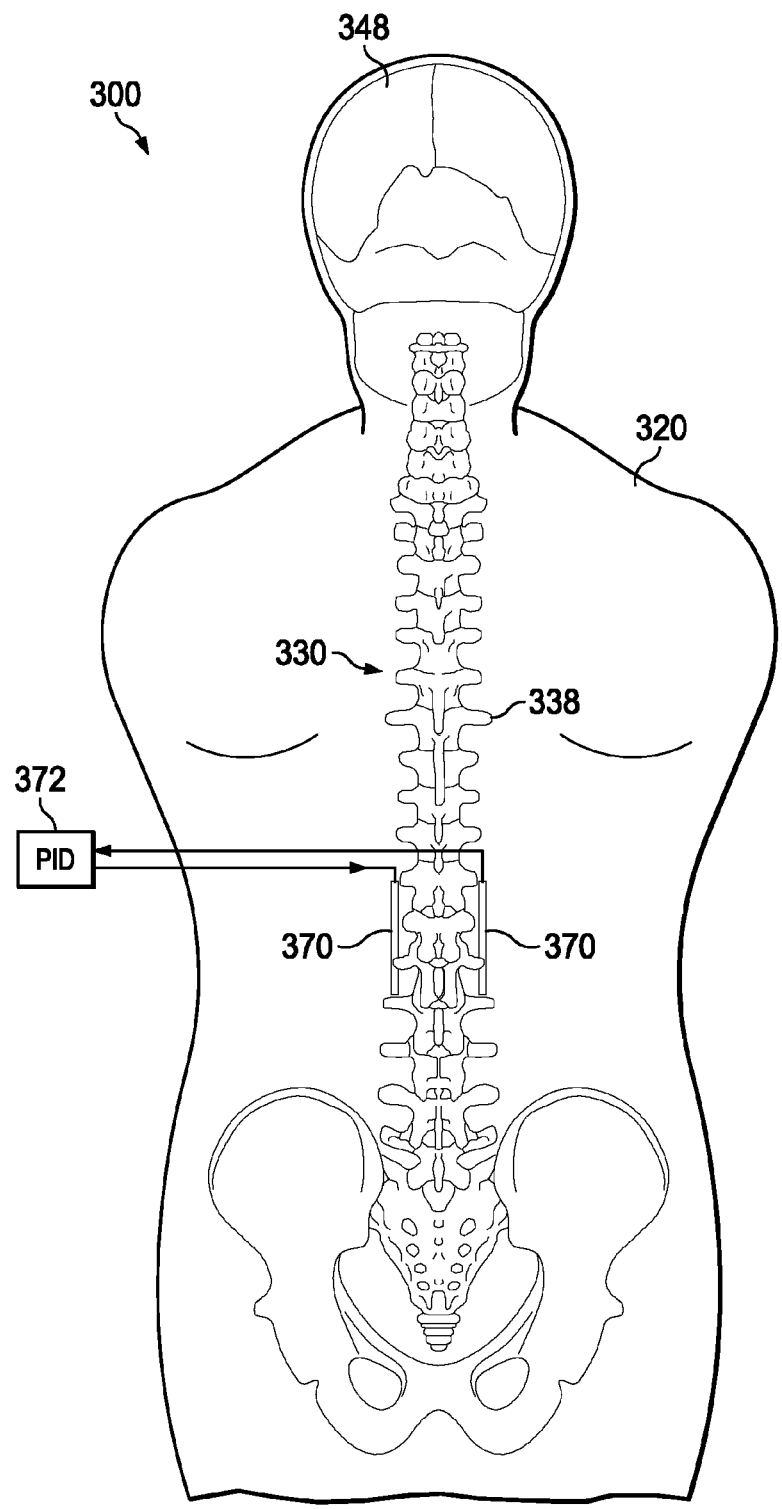
FIG. 4 is a top view illustrating one placement of heat sources in the spinal injection trainer of FIG. 3.

FIG. 4 is a top view of spinal model 300 wherein heaters 370 have been placed adjacent the spinal region where needle practice occurs. Heaters 370 are utilized to heat localized areas of synthetic gel matrix 320 to a temperature approaching the melting point of the matrix material. As the matrix material approaches the melting point, the synthetic gel matrix 320 softens and needle tracks in the heated area fuse and close, eliminating the needle tracks. In one variation, heaters 370 are cartridge heaters which may be placed on either side vertebral column 330 in an area utilized for needle practice. The cartridge heaters are preferably controlled by a PID controller 372 that can maintain a programmed temperature to within −0.5 to +0.5 degrees Celsius. PID control permits more stable temperature range management than other types of temperature control such as on/off control, or proportional control.

Suitable PID controllers for the invention include, but are not limited to auto-tune type controllers such as the EZ-ZONE PM Temperature Controller Series from Watlow Inc., 12001 Lackland Rd., St. Louis, Mo., USA, 63146, that provide for adaptive temperature sensing and learning, whereby the controller initially probes a material to determine its thermal properties which are then employed in the controller's PID algorithm. When it is desired that the needle tracks be erased, the controller can be set to cycle to a desired temperature that is where the synthetic gel matrix starts to transition to a flowable or liquid state, whereby the tracks are fused closed, after which the cartridge heaters cycle off. Cartridge heaters 370 are controlled such that the heaters do not exceed the melting point of the synthetic gel matrix material.

Figure 5:
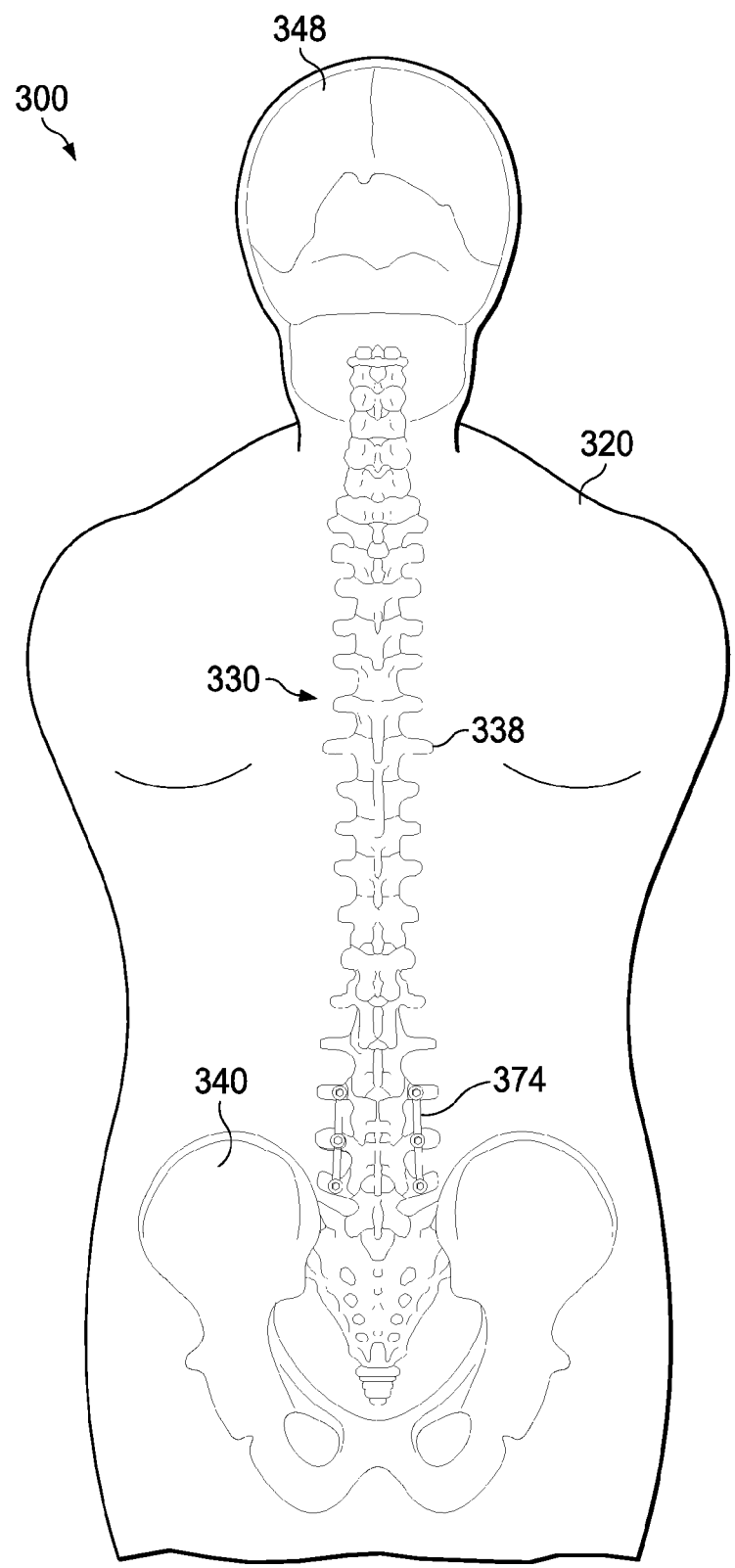
FIG. 5 is a top view illustrating one placement of surgical hardware on the spinal column.

FIG. 5 is a top view of spinal model 300 including surgical hardware 374 installed on the embedded vertebral column 330. Spinal fusion surgery is a procedure wherein some or all of one or more vertebral discs are removed and replace with bone grafts. Metallic rods, brackets, clamps and threaded fasteners, such as surgical hardware 374 are used to keep the vertebra and grafts in place while the graft and bones grow together or fuse. However, surgical hardware 374 can mask or distort adjacent regions during imaging such that distinguishing spinal structures may be difficult. In order to provide an accurate postoperative assessment of spinal surgical hardware, practitioners should be familiar with the normal imaging appearances of the lumbar spine after procedures such as stabilization, fusion, and disc replacement. Spinal model 300 with surgical hardware 374 provides a means to familiarize practitioners with the visual and imaged normal appearance of vertebral column 330 spine after implantation of the surgical hardware. Spinal model 300 with surgical hardware 374 also provides a means of needle insertion practice training for cases where surgical hardware has been installed.

Figure 6:
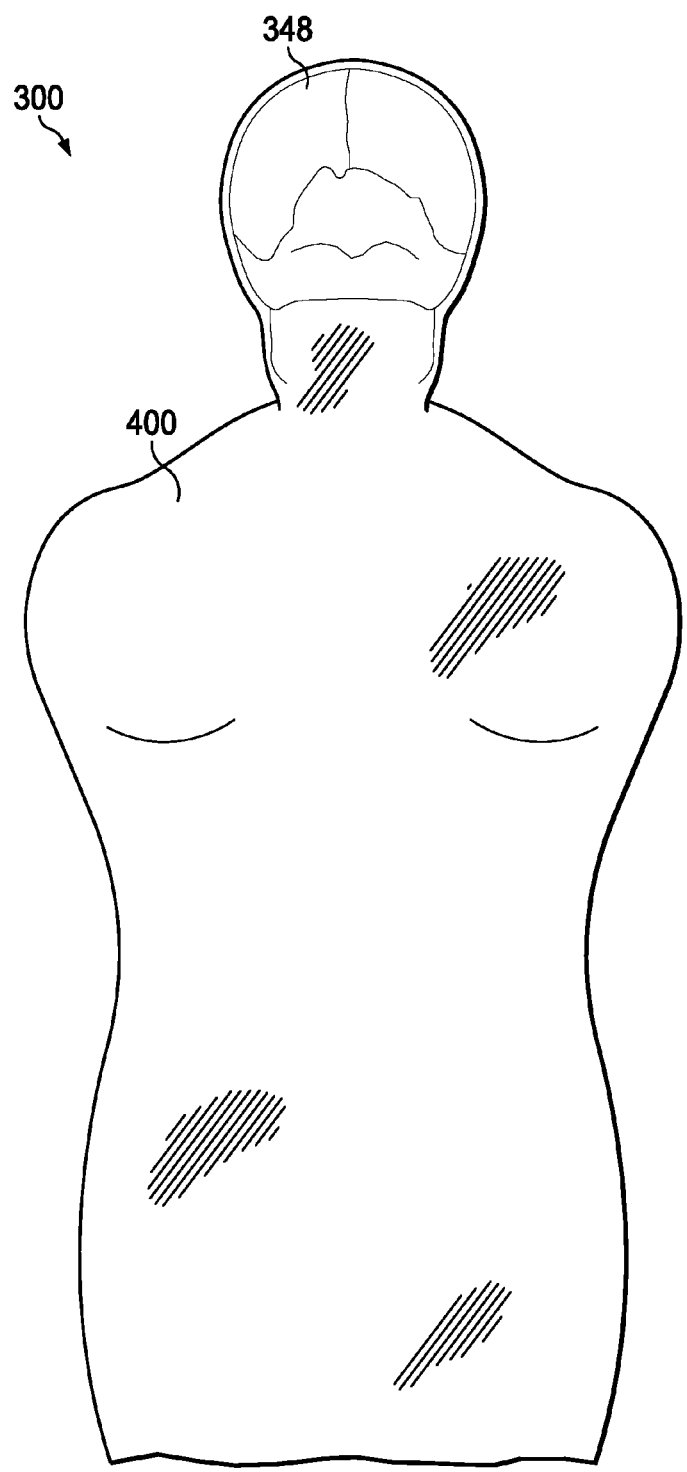
FIG. 6 shows the embodiment of FIG. 1 with a sheet placed over the contoured form.

FIG. 6 is a top view of model 300 partially covered with a flexible opaque sheet 400. Sheet 400 may be sized and shaped to fit the model and formed from a silicone or similar elastomer having a texture similar to human skin with a thickness of from about 2 mm to about 10 mm. In one embodiment, sheet 400 may be removable and fitted over model 300 when desired. In different embodiments, sheet 400 may be affixed to model 300 with an adhesive or otherwise attached to the model or molded onto the model by placing the sheet in mold 110 prior to placing the synthetic gel matrix material into the mold.

Sheet 400 allows for "blind" palpation and discernment of the spinous process 342 (FIG. 3) to simulate a clinical setting. Flexible opaque sheet 400 may be used during needle insertion practice with or without fluoroscopy. While the use of opaque sheet 400 prevents visual observation of needle 350 (FIG. 3) during insertion, use of the sheet during needle insertion provides a more realistic simulation of actual practice on a live patient. Likewise, while the use of opaque sheet 400 during spinal palpation practice prevents visual observation of vertebral column 130 during the practice, the use of the sheet provides a more realistic simulation of an actual procedure.

Figure 7:
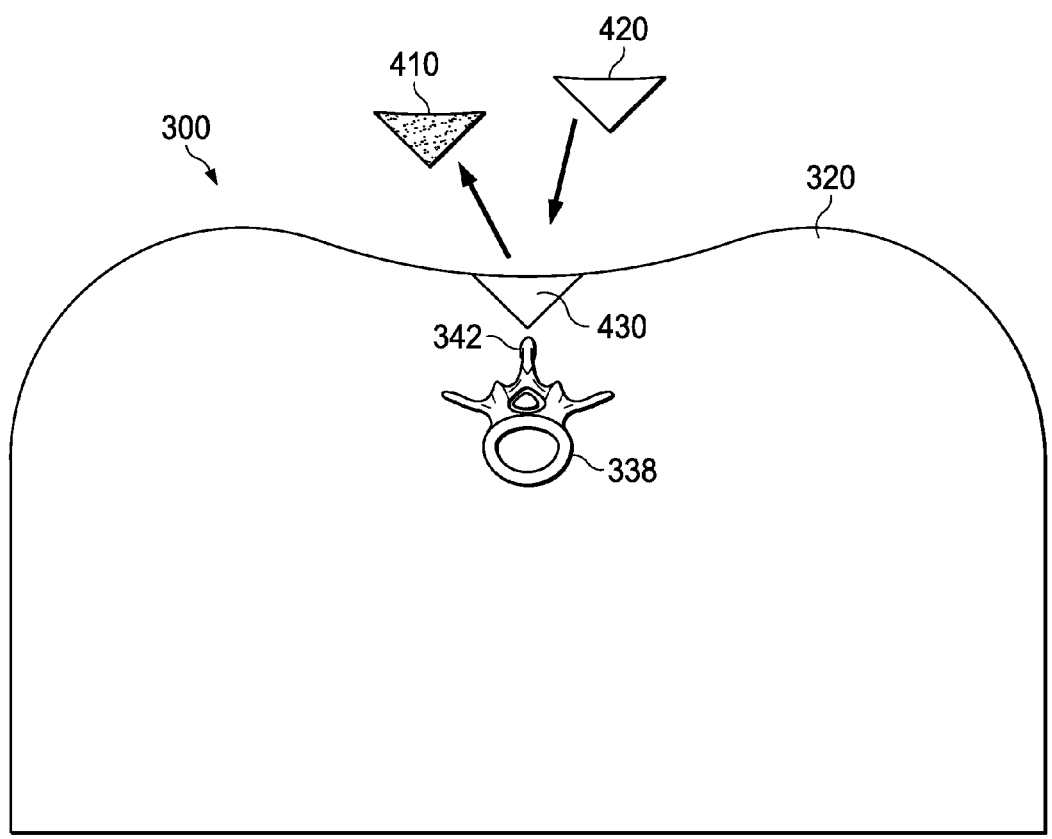
FIG. 7 is a cross-sectional view taken along lines 7-7 of the embodiment shown in FIG. 1 illustrating replacement of a portion of the model.

In some instances it may be desirable to replace a portion of synthetic gel matrix 320 without replacing the entire matrix, for example, if a portion of synthetic gel matrix 320 becomes discolored due to contamination or due to repeated reheating with heaters 370 (FIG. 4). FIG. 7 is a partial cross sectional view of model 300 illustrating a partial replacement of synthetic gel matrix 320. As illustrated, a discolored section 410 of synthetic gel matrix 320 is separated by cutting and removing the section from model 300. A replacement section 420 of synthetic gel is cut to fit the cavity or opening 430 created by the removal of section 410. The replacement section 420 is fitted into cavity 430 and heated to fuse the section into model 300. A localized area of model 300 may be heated to fuse replacement section 420 into model 300 with, for example, heaters 370 or another heat source. Alternatively, the entire model 300 may be placed into an over or similar enclosure and the model heated to fuse replacement section 420 in place. In either case, the replacement section and the adjacent portion of model 300 are heated to a temperature approaching, but not exceeding, the melting point of the synthetic gel matrix 320 to fuse the replacement section 420 to model 300.

Although the models described and illustrated herein include a human vertebral column, models of different portions of human anatomy with different skeletal structures may be constructed. For example, a model of a human leg, arm foot or other body portion may be formed from a thermoplastic elastomer matrix as described above with embedded natural or synthetic bones and/or synthetic soft tissue structures to provide a practice model for injections and arthroscopic surgery. Such models may also be provided with embedded light sources, radiopaque markers or targets and/or surgical hardware. Models may also be constructed for veterinary applications.

Accordingly, a model for anatomic training includes a visibly clear thermoplastic elastomer matrix having at least one contoured surface that simulates at least a portion of a human body and provides tactile feedback similar to human tissue. The visibly clear thermoplastic elastomer matrix provides visible needle tracks upon needle penetration that are fused closed upon heating the thermoplastic elastomer matrix such that the needle tracks are no longer visible in the thermoplastic elastomer matrix. Selected portions of the model may be replaced by removing the selected portion of the visibly clear thermoplastic elastomer matrix, replacing the removed selected portion of the visibly clear thermoplastic elastomer matrix with a new replacement portion and applying heat to fuse the replacement portion into the model. A skeletal structure is embedded within the visibly clear thermoplastic elastomer matrix at the same location, relative to the contoured surface, as the corresponding skeletal structure is located in a human body. The skeletal structure may be a vertebral column with synthetic simulated soft tissue structures such as simulated discs positioned between vertebra and a simulated spinal cord and nerves. The skeletal structure produces a fluoroscopic image representative of human bone corresponding to the skeletal structure. A light source such as a plurality of LEDS is embedded in the visibly clear thermoplastic elastomer matrix adjacent to at least a portion of the skeletal structure, increasing the visibility of needle tracks formed in the visibly clear thermoplastic elastomer matrix. At least one heat source embedded in the visibly clear, thermoplastic elastomer matrix adjacent the vertebral column provides localized heating of a portion of the visibly clear thermoplastic elastomer matrix to fuse needle tracks formed in the matrix. In different embodiments, the model includes surgical hardware installed on the embedded vertebral column. Radiopaque markers may be embedded in the visibly clear thermoplastic elastomer matrix adjacent selected portions of the skeletal structure. The visibly clear thermoplastic matrix may include from about 15 wt % to about 20 wt % of a rubbery block copolymer such as an SEBS (styrene-ethylene/butylene-styrene) block copolymer and from about 80 wt % to about 85 wt % of a white oil. In one embodiment, the rubbery block copolymer has a tensile stress of from about 8.00 to about 10 psi, a tensile strength at break of from about 140 to about 170 psi and a tensile elongation at break of from about 500 to about 1500%.

It will be appreciated by those skilled in the art having the benefit of this disclosure that the spinal injection trainer and method described herein may be configured for multiple adaptations based on selected criteria. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A model for anatomic training, comprising:
a visibly clear thermoplastic elastomer matrix formed with at least one contoured surface, the contoured surface simulating at least a portion of a human body, the visibly clear thermoplastic elastomer matrix providing visible needle tracks resulting from needle penetration and extraction of a needle along the path of the needle after insertion at a point on the contoured surface to a target below the contoured surface, at least a portion of the needle tracks extending along the path remaining visible until the needle tracks are fused closed with a heat source, whereby the needle tracks are fused closed upon heating the thermoplastic elastomer matrix such that the needle tracks are no longer visible in the thermoplastic elastomer matrix; and
a skeletal structure embedded within the visibly clear thermoplastic elastomer matrix at the same location, relative to the contoured surface, as the corresponding skeletal structure is located in a human body, at least a portion of the skeletal structure producing a fluoroscopic image with an image contrast representative of the structure of human bone corresponding to the at least a portion of the skeletal structure.

2. The model of claim 1 wherein the visibly clear thermoplastic elastomer matrix provides tactile feedback substantially similar to human tissue.

3. The model of claim 1 wherein a selected portion of the model is replaceable by removing a selected portion of the visibly clear thermoplastic elastomer matrix, replacing the removed selected portion of the visibly clear thermoplastic elastomer matrix with a new replacement portion and applying heat to fuse the replacement portion into the model.

4. The model of claim 1 further comprising a light source embedded in the visibly clear thermoplastic elastomer matrix, the light source increasing the visibility of needle tracks formed in the visibly clear thermoplastic elastomer matrix.

5. The model of claim 4 wherein the light source comprises a plurality of LEDs.

6. The model of claim 4 wherein the light source is embedded in the visibly clear thermoplastic elastomer matrix adjacent at least a portion of the skeletal structure.

7. The model of claim 1 further comprising at least one heat source embedded in the visibly clear, thermoplastic elastomer matrix, the heat source providing localized heating of a portion of the visibly clear thermoplastic elastomer matrix to fuse needle tracks formed in the matrix.

8. The model of claim 1 wherein the at least a portion of the skeletal structure comprises a vertebral column.

9. The model of claim 8 further comprising surgical hardware installed on the embedded vertebral column.

10. The model of claim 8 further comprising at least one heat source embedded in the synthetic gel matrix adjacent at least a portion of the embedded vertebral column.

11. The model of claim 1 further comprising radiopaque markers embedded in the visibly clear thermoplastic elastomer matrix adjacent selected portions of the skeletal structure.

12. The model of claim 1 further comprising a form having contoured portions simulating surfaces of at least a portion of a human body.

13. The model of claim 1 wherein the at least a portion of the skeletal structure is comprised of natural bone.

14. The model of claim 1 wherein the visibly clear thermoplastic matrix comprises from about 15 wt % to about 20 wt % of a rubbery block copolymer and from about 80 wt % to about 85 wt % of a white oil.

15. The model of claim 14 wherein the rubbery block copolymer comprises an SEBS (styrene-ethylene/butylene-styrene) block copolymer.

16. The model of claim 14 wherein the rubbery block copolymer has a tensile stress of from about 8.00 to about 10 psi, a tensile strength at break of from about 140 to about 170 psi and a tensile elongation at break of from about 500 to about 1500%.

17. The model of claim 1 wherein the at least a portion of the skeletal structure is comprised of human bone.

18. A model for anatomic training, comprising:
a visibly clear thermoplastic elastomer matrix formed with at least one contoured surface, the contoured surface simulating at least a portion of a human body, the visibly clear thermoplastic elastomer matrix providing visible needle tracks resulting from needle penetration and extraction of a needle along the path of the needle after insertion at a point on the contoured surface to a target below the contoured surface, at least a portion of the needle tracks extending along the path remaining visible until the needle tracks are fused closed with a heat source, whereby the needle tracks are fused closed upon heating the thermoplastic elastomer matrix such that the needle tracks are no longer visible in the thermoplastic elastomer matrix; and
a skeletal structure embedded within the visibly clear thermoplastic elastomer matrix at the same location, relative to the contoured surface, as the corresponding skeletal structure is located in a human body, and
at least a first portion of the skeletal structure comprising a fluoroscopic material producing a fluoroscopic image with an image contrast representative of the structure of human bone, and
at least a second portion of the skeletal structure comprising a non-fluoroscopic material producing a fluoroscopic image with an image contrast representative of the structure of the human soft tissue.

19. The model of claim 18 wherein the simulated soft tissue structure comprises at least one synthetic intervertebral disc.

20. The model of claim 18 wherein the simulated soft tissue structure comprises a synthetic simulated spinal cord.

\* \* \* \* \*